(12) United States Patent
Liu et al.

(10) Patent No.: US 11,733,230 B2
(45) Date of Patent: Aug. 22, 2023

(54) METHOD FOR QUICKLY AND ACCURATELY ANALYZING POLYPHENOL CONTENT IN RAPESEED OIL

(71) Applicant: Jiangnan University, Wuxi (CN)

(72) Inventors: Yuanfa Liu, Wuxi (CN); Junge Song, Wuxi (CN); Yongjiang Xu, Wuxi (CN); Zhaojun Zheng, Wuxi (CN); Chen Cao, Wuxi (CN); Yinghong Zhai, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 407 days.

(21) Appl. No.: 17/139,084

(22) Filed: Dec. 31, 2020

(65) Prior Publication Data

US 2021/0123897 A1    Apr. 29, 2021

Related U.S. Application Data

(63) Continuation of application No. PCT/CN2019/113576, filed on Oct. 28, 2019.

(30) Foreign Application Priority Data

Mar. 14, 2019  (CN) .......................... 201910194098.1

(51) Int. Cl.
*G01N 33/03* (2006.01)
*B01D 11/04* (2006.01)
(Continued)

(52) U.S. Cl.
CPC .......... *G01N 33/03* (2013.01); *B01D 11/048* (2013.01); *B01D 11/0492* (2013.01);
(Continued)

(58) Field of Classification Search
CPC ...... G01N 33/03; G01N 1/4022; G01N 1/405; G01N 1/4055; G01N 30/06;
(Continued)

(56) References Cited

FOREIGN PATENT DOCUMENTS

| CN | 1506680 A | 6/2004 |
|----|-----------|--------|
| CN | 103819311 A | 5/2014 |

(Continued)

OTHER PUBLICATIONS

Capriotti, Anna Laura, et al. "Comparison of extraction methods for the identification and quantification of polyphenols in virgin olive oil by ultra-HPLC-QToF mass spectrometry." Food Chemistry 158 (2014): 392-400. (Year: 2014).*

(Continued)

*Primary Examiner* — Jennifer Wecker
*Assistant Examiner* — Michael Paul Shimek
(74) *Attorney, Agent, or Firm* — IPro, PLLC; Na Xu

(57) ABSTRACT

The disclosure discloses a method for quickly and accurately analyzing polyphenol content in rapeseed oil, and belongs to the field of analysis of natural compounds. The separation method of the disclosure uses acetonitrile-water as an extractant to extract polyphenols from the rapeseed oil, and cooperates with a $C_{18}$ adsorbent for purification, and then performs separation and purification. Compared with the traditional liquid-liquid extraction and solid-phase extraction, the method has an average recovery rate of polyphenols in the rapeseed oil of 81.31% to 102.95%, and RSDs of 0.86% to 8.03%, and has higher accuracy and precision. The method of the disclosure not only uses less organic reagents and causes less environmental pollution, but also reduces matrix interference and improves purification efficiency through optimization of the adsorbent. The method of the disclosure not only is simple to operate and low in cost, but also has less matrix interference and accurate results, and is suitable for the qualitative and quantitative determination of polyphenols in the rapeseed oil.

14 Claims, 2 Drawing Sheets

(51) Int. Cl.
*G01N 1/40* (2006.01)
*G01N 30/06* (2006.01)
*G01N 30/72* (2006.01)
*G01N 30/02* (2006.01)

(52) U.S. Cl.
CPC ........... *G01N 1/405* (2013.01); *G01N 1/4022* (2013.01); *G01N 1/4055* (2013.01); *G01N 30/06* (2013.01); *G01N 30/7233* (2013.01); *G01N 2001/4061* (2013.01); *G01N 2030/027* (2013.01); *G01N 2030/065* (2013.01)

(58) Field of Classification Search
CPC ....... G01N 30/7233; G01N 2001/4061; G01N 2030/027; G01N 2030/065; B01D 11/048; B01D 11/0492; B01J 20/281
See application file for complete search history.

(56) References Cited

FOREIGN PATENT DOCUMENTS

| | | |
|---|---|---|
| CN | 104330498 A | 2/2015 |
| CN | 109307717 A | 2/2019 |
| CN | 109884207 A | 6/2019 |

OTHER PUBLICATIONS

K. Sharmili et al. "Development. Optimization and Validation of QuEChERS Based Liquid Chromatography Tandem Miass Spectrometry Method for Determination of Multimycotoxin in Vegetable Oil"Food Control, vol. 70, Apr. 22, 2016 (Apr. 22, 2016).

Li. Lingyun et al., Detection of Residue of Carbamate Pesticides in Grain, Oil Materials and Vegetable Oil by UPLC-MS/MS), Quality and Safety of Agro-Products,No. 5, Dec. 31, 2018 (Dec. 31, 2018).

* cited by examiner

METHOD FOR QUICKLY AND ACCURATELY ANALYZING POLYPHENOL CONTENT IN RAPESEED OIL

TECHNICAL FIELD

The disclosure belongs to the field of analysis of natural compounds, and specifically relates to a method for quickly and accurately analyzing polyphenol content in rapeseed oil.

BACKGROUND

Polyphenols are widely found in plants and are an important secondary metabolite in plants. Its molecular structure contains several phenolic hydroxyl groups. Studies have confirmed that polyphenols have physiological functions and biological activities such as tumor resistance, blood sugar lowering, bacteria resistance, oxidation resistance, and free radical scavenging, and have broad development prospects. Polyphenol content in rapeseed is much higher than that in other oil crops, but most of polyphenols remain in the rapeseed meal during oil production, and only a small part will be transferred to rapeseed oil. Since polyphenols can improve the oxidative stability and nutritional quality of the rapeseed oil, if the composition and content of polyphenols in the rapeseed oil can be accurately analyzed, it will be of great significance to the processing of the rapeseed oil.

At present, liquid-liquid extraction and solid-phase extraction are commonly used to extract polyphenols from vegetable oils. However, these two methods have disadvantages such as cumbersome operation, high consumption of organic solvents, and high content of matrix co-extracts. Therefore, it is necessary to find a simple and environment-friendly method that can significantly reduce the content of the matrix co-extracts.

SUMMARY

The disclosure discloses a method for extracting polyphenols from rapeseed oil, including:

(1) extracting the rapeseed oil by using a mixed solution of acetonitrile and water as an extractant, performing solid-liquid separation, and collecting a supernatant to obtain an extracting solution; and (2) adding 25 to 35 mg/mL $C_{18}$ adsorbent to the extracting solution obtained in step (1), and performing separation to remove solid components to obtain a polyphenol solution.

In one embodiment of the disclosure, a volume ratio of acetonitrile to water in the extractant is (4 to 8):1.

In one embodiment of the disclosure, a mass-volume ratio of rapeseed oil to extractant in the step (1) is 0.25 to 0.35 g/mL.

In one embodiment of the disclosure, the step (1) further includes adding anhydrous $MgSO_4$ and NaCl to cooperate with the extractant.

In one embodiment of the disclosure, a mass ratio of anhydrous $MgSO_4$ to NaCl is 2:1 to 6:1.

In one embodiment of the disclosure, the step (1) further includes performing freezing treatment on the collected supernatant to obtain the extracting solution. The conditions of the freezing treatment are as follows: the temperature is $-15°$ C. to $-20°$ C., and the time is 1.5 to 2.5 h.

In one embodiment of the disclosure, step (2) further includes adding anhydrous $MgSO_4$ to be used in combination with the adsorbent, so as to further remove moisture and fatty impurities in the extracting solution to obtain the polyphenol solution.

In one embodiment of the disclosure, the separation is performing centrifugal separation on extract liquor at a rotational speed of 3,000 to 5,000 rpm.

The disclosure further discloses a method for detecting polyphenols in vegetable oil. The method includes pre-treating the vegetable oil in advance to obtain a polyphenol solution and then performing detection. The pre-treatment method is the above-mentioned method for extracting polyphenols from the rapeseed oil.

In one embodiment of the disclosure, the method further includes concentrating the polyphenol solution, and then dissolving it with a solvent to obtain a detection sample solution, which can be used for detection.

In one embodiment of the disclosure, the solvent includes methanol.

The disclosure further discloses a method for detecting polyphenols in vegetable oil by liquid chromatography. The method includes pre-treating the vegetable oil in advance to obtain a liquid sample of polyphenols, and then performing liquid chromatography detection. The pre-treatment method is the above-mentioned method.

In one embodiment of the disclosure, the chromatographic column of the liquid chromatography is Thermo Hypersil GOLD (100 mm×2.1 mm, 1.9 μm), and the column oven temperature is 30 to 40° C.

In one embodiment of the disclosure, a mobile phase A of the liquid chromatography is a 0.1% aqueous acetic acid solution, a mobile phase B is an acetonitrile solution, and a flow rate is 0.2 to 0.5 mL/min.

The disclosure discloses the method for quickly and accurately analyzing polyphenol content in the rapeseed oil. The method includes: extracting polyphenols from rapeseed oil with acetonitrile-water, purifying with the adsorbent $C_{18}$, and performing separation and purification to remove the solid components, so as to obtain polyphenol sample liquid; and then performing liquid chromatography detection. Compared with the traditional liquid-liquid extraction and solid-phase extraction, the method has an average recovery rate of polyphenols in the rapeseed oil of 81.31% to 102.95%, and RSDs of 0.86% to 8.03%, and has higher accuracy and precision. The method of the disclosure not only uses less organic reagents and causes less environmental pollution, but also reduces matrix interference and improves purification efficiency through optimization of the adsorbent. The method of the disclosure not only is simple to operate and low in cost, but also has less matrix interference and accurate results, and is suitable for the qualitative and quantitative determination of polyphenols in the rapeseed oil.

DETAILED DESCRIPTION

Figure 1:
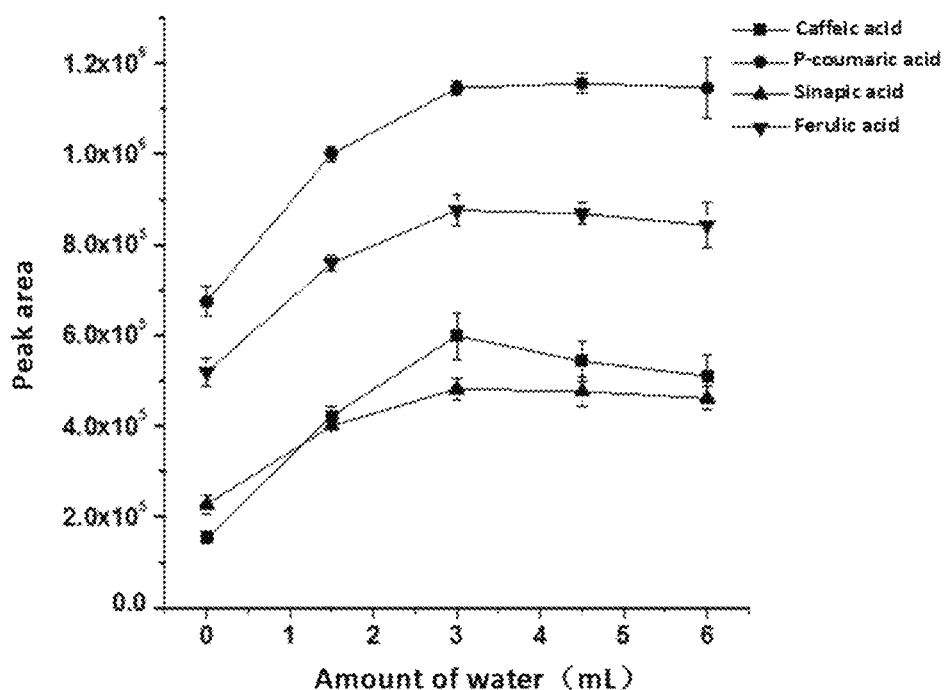
FIG. 1 is a diagram of the influence of the amount of water on the extraction effect of polyphenols by using Example 1 as a reference.
Figure 2:
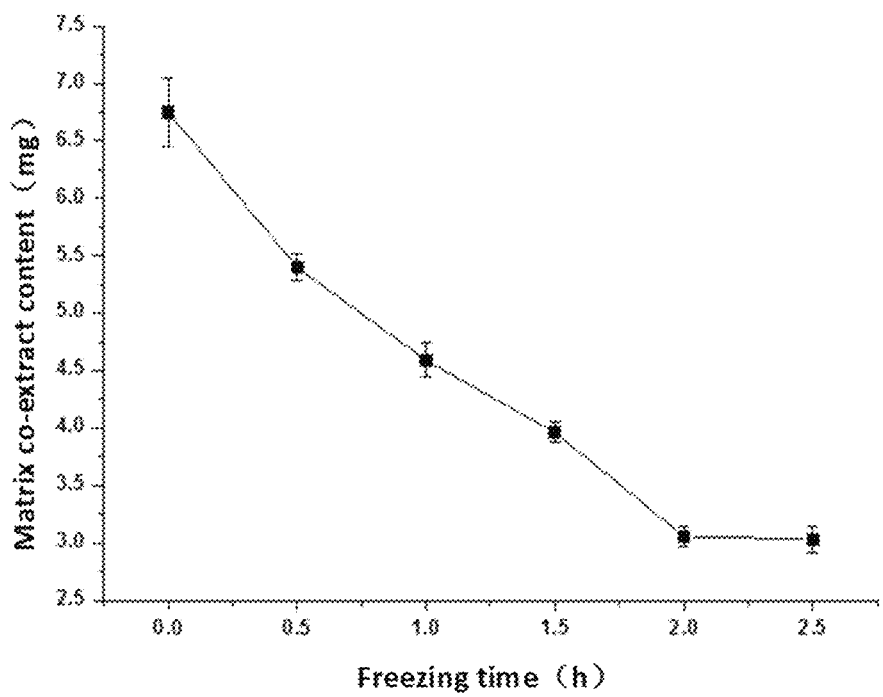
FIG. 2 is a diagram of the influence of freezing time on the content of matrix co-extracts by using Example 1 as a reference.
Figure 3:
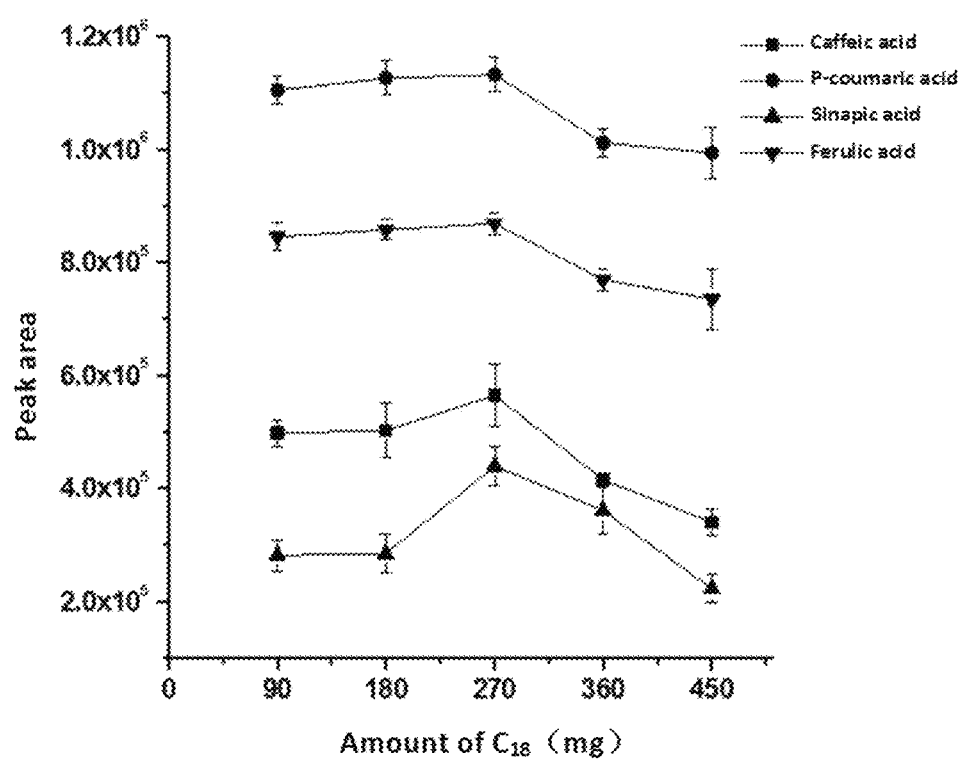
FIG. 3 is a diagram of the influence of the amount of $C_{18}$ on the extraction effect of polyphenols by using Example 1 as a reference.

The following examples are used to illustrate the disclosure, but not to limit the scope of the disclosure.

Example 1: Method for Extracting Polyphenols from Rapeseed Oil

Separation treatment: 6.00 g of rapeseed oil was accurately weighed and put into a 50 mL centrifuge tube, 3 mL of water and 18 mL of acetonitrile were added, and shaking was performed for 5 min. 7.2 g of anhydrous $MgSO_4$ and 1.8 g of NaCl were added, shaking was performed for 2 min, and then centrifugation was performed for 5 min at 4,000 rpm. A supernatant was transferred to a centrifuge tube and frozen for 2 h at −20° C. 9 mL of supernatant was transferred to a 15 mL centrifuge tube, 270 mg of $C_{18}$ and 1.8 g of anhydrous $MgSO_4$ were added, shaking was performed for 2 min, and then centrifugation was performed for 5 min at 4,000 rpm. A supernatant, namely, a polyphenol solution, was obtained.

Example 2: Method for Detecting Polyphenols in Vegetable Oil

Conditions of liquid chromatography: The chromatographic column was Thermo Hypersil GOLD (100 mm×2.1 mm, 1.9 μm); the column oven temperature was 35° C.; the sample size was 2 μL; the flow rate was 0.30 mL/min; the mobile phase A was a 0.1% aqueous acetic acid solution; and the mobile phase B was an acetonitrile solution.

(1) Preparation of standard solution: a polyphenol mixed standard solution with a concentration of 200 μg/mL was prepared by using chromatographic grade methanol, and then stored at −20° C. before use. A working solution was prepared by diluting a stock solution with methanol.

(2) Separate determination after diluting standard solution into working solutions of different concentrations with methanol: each concentration was determined 3 times in parallel to obtain linear equations and correlation coefficients of polyphenols. The method detection limit was calculated by 3 times the signal-to-noise ratio, and the method quantification limit was calculated by 10 times the signal-to-noise ratio. The results are shown in Table 1.

(3) 4.5 mL of supernatant (the polyphenol solution obtained in Example 1) was accurately transferred into a nitrogen blowpipe, slowly blown dry in a nitrogen blower, added with 1.5 mL of methanol solution, and filtered with a 0.22 μm filter membrane into a sample bottle for HPLC-MS determination.

(4) Standard addition recovery rate: 10 μg/g of the standard was added to an actual sample for determination, the process was repeated for 3 times, and the average recovery rate and relative standard deviation (RSD) were calculated. The results are shown in Table 2.

TABLE 2

Determination of standard addition recovery rate

| Compound | Standard addition recovery rate |
| --- | --- |
| Protocatechuic acid | 86.17[a] ± 8.03[b] |
| P-hydroxybenzoic acid | 99.23 ± 4.83 |
| Caffeic acid | 91.06 ± 4.13 |
| Vanillic acid | 99.53 ± 3.33 |
| Syringic acid | 100.34 ± 0.86 |
| P-coumaric acid | 99.71 ± 1.48 |
| Sinapic acid | 101.90 ± 3.24 |
| Ferulic acid | 102.95 ± 1.74 |
| Cinnamic acid | 81.31 ± 2.95 |
| Sinapine | 97.96 ± 7.90 |

[a] represents an average recovery rate, %; and
[b] represents a relative standard deviation (RSD, %).

Example 3

Referring to Example 1, the extractant was replaced with 7 mL of water and 14 mL of acetonitrile (acetonitrile/water: 2:1), 4.2 mL of water and 16.8 mL of acetonitrile (4:1), and 2.3 mL of water and 18.7 mL of acetonitrile (acetonitrile/water: 8:1), respectively, and other conditions remained unchanged. The obtained supernatant was detected by liquid chromatography, and the average peak area and RSD were calculated. The obtained results are shown in Table 3.

TABLE 1

Determination of linear range, detection limit and quantification limit

| Compound | Regression equation | Correlation coefficient $R^2$ | Linear range (μg/mL) | LOD (μg/mL) | LOQ (μg/mL) |
| --- | --- | --- | --- | --- | --- |
| Protocatechuic acid | Y = 3.0872x + 0.0976 | 0.9961 | 0.04-10 | 0.010 | 0.033 |
| P-hydroxybenzoic acid | Y = 5.0126x + 1.2662 | 0.9955 | 0.04-10 | 0.010 | 0.033 |
| Caffeic acid | Y = 0.1727x − 0.0290 | 0.9977 | 0.30-10 | 0.080 | 0.267 |
| Vanillic acid | Y = 0.6213x + 0.3024 | 0.9964 | 0.03-10 | 0.008 | 0.027 |
| Syringic acid | Y = 1.0651x + 0.2823 | 0.9935 | 0.03-10 | 0.008 | 0.027 |
| P-coumaric acid | Y = 3.0005x + 0.9064 | 0.9925 | 0.02-10 | 0.006 | 0.020 |
| Sinapic acid | Y = 0.2064x + 0.0778 | 0.9902 | 0.03-10 | 0.008 | 0.027 |
| Ferulic acid | Y = 2.7085x + 1.2602 | 0.9945 | 0.02-10 | 0.004 | 0.013 |
| Cinnamic acid | Y = 4.7007x + 2.4276 | 0.9924 | 0.01-10 | 0.002 | 0.007 |
| Sinapine | Y = 9.9452x + 6.1696 | 0.9923 | 0.02-10 | 0.004 | 0.013 |

TABLE 3

Detection results of sample prepared in Example 3

| Volume ratio of acetonitrile to water | Caffeic acid/peak area (% RSD) | P-coumaric acid/peak area (% RSD) | Sinapic acid/peak area (% RSD) | Ferulic acid/peak area (% RSD) |
|---|---|---|---|---|
| 2:1 | 226120(10.88) | 733015(2.21) | 333725(6.38) | 533467(5.35) |
| 4:1 | 379940(11.52) | 1021980(6.71) | 404765(10.75) | 767575(9.67) |
| 6:1 | 564683(9.93) | 1132224(2.74) | 439369(7.74) | 868811(2.18) |
| 8:1 | 531352(12.44) | 1128797(4.33) | 426528(10.09) | 866902(8.02) |

Example 4

Referring to Example 1, the amount of the extractant was replaced with 4.5 mL of water and 27 mL of acetonitrile, and 2.25 mL of water and 13.5 mL of acetonitrile, respectively, and other conditions remained unchanged. The obtained supernatant was detected by liquid chromatography, and the average peak area and RSD were calculated. The obtained results are shown in Table 4.

TABLE 4

Detection results of sample prepared in Example 4

| Extractant | Caffeic acid/peak area (% RSD) | P-coumaric acid/peak area (% RSD) | Sinapic acid/peak area (% RSD) | Ferulic acid/peak area (% RSD) |
|---|---|---|---|---|
| 2.25 mL of water and 13.5 mL of acetonitrile | 288232(12.03) | 966108(4.70) | 344566(9.57) | 716155(3.28) |
| 3 mL of water and 18 mL of acetonitrile | 564683(9.93) | 1132224(2.74) | 439369(7.74) | 868811(2.18) |
| 4.5 mL of water and 27 mL of acetonitrile | 462570(10.47) | 1110167(2.55) | 422409(4.10) | 821657(5.87) |

Example 5

Referring to Example 1, the amount of the adsorbent was replaced with 90 mg, 180 mg, 360 mg, and 450 mg, respectively, and other conditions remained unchanged. The obtained supernatant was detected by liquid chromatography, and the average peak area and RSD were calculated. The obtained results are shown in Table 5.

TABLE 5

Detection results of sample prepared in Example 5

| Amount of $C_{18}$/mg | Caffeic acid/peak area (% RSD) | P-coumaric acid/peak area (% RSD) | Sinapic acid/peak area (% RSD) | Ferulic acid/peak area (% RSD) |
|---|---|---|---|---|
| 90 | 497706(4.82) | 1104624(2.35) | 281526(10.04) | 845011(2.86) |
| 180 | 502562(9.83) | 1126695(2.69) | 284957(11.98) | 857426(2.05) |
| 270 | 564683(9.93) | 1132224(2.74) | 439369(7.74) | 868811(2.18) |
| 360 | 415247(2.43) | 1011740(2.39) | 360893(11.75) | 769054(2.45) |
| 450 | 339775(6.87) | 993345(4.56) | 222556(11.03) | 734897(7.35) |

Comparative Example 1

Extraction of polyphenols by liquid-liquid extraction technology: 2.50 g of rapeseed oil was accurately weighed, dissolved in 3 mL of n-hexane, and shaken for 1 min. Extraction was performed with 3 mL of methanol solution with a volume fraction of 80% for 3 times, shaking was performed for 5 min each time, and centrifugation was performed for 5 min at 4,000 rpm. The methanol extracting solutions were combined, the extracting solution was slowly blown dry in a nitrogen blower, added with 2.5 mL of methanol solution, and filtered with a 0.22 μm filter membrane, and a filtrate was collected into a sample bottle.

The method for determining the polyphenol content by using HPLC-MS was the same as the liquid chromatography conditions and steps (1) to (3) of Example 2. The analysis results are shown in Table 6.

Comparative Example 2

Extraction of polyphenols by solid-phase extraction technology: a glycol-based solid-phase extraction column was placed in a solid-phase extraction device, and an SPE column was activated with 5 mL of methanol and 5 mL of n-hexane, respectively. 1.50 g of rapeseed oil was accurately weighed, dissolved in 5 mL of n-hexane, and shaken for 1 min. A sample was loaded into the column, washed with 5 mL of n-hexane and 5 mL of a mixture of n-hexane and ethyl acetate (a ratio of n-hexane to ethyl acetate is 90:10, v/v) by column chromatography sequentially, and finally eluted with 5 mL of methanol solution, an eluate was collected, slowly blown dry in a nitrogen blower, added with 1.5 mL of methanol solution, and filtered with a 0.22 μm filter membrane, and a filtrate was collected into a sample bottle.

The method for determining the polyphenol content by using HPLC-MS was the same as the liquid chromatography conditions and steps (1) to (3) of Example 2. The analysis results are shown in Table 6.

TABLE 6

Detection results of samples prepared in Comparative Examples 1 and 2

| Compound | Comparative Example 1 | Comparative Example 2 | Example 1 |
| --- | --- | --- | --- |
| Protocatechuic acid | 82.53 ± 5.26 | 65.85 ± 3.05 | 86.17 ± 8.03 |
| P-hydroxybenzoic acid | 76.90 ± 7.82 | 77.95 ± 10.13 | 99.23 ± 4.83 |
| Caffeic acid | 81.28 ± 8.81 | 56.98 ± 9.23 | 91.06 ± 4.13 |
| Vanillic acid | 62.16 ± 4.05 | 52.32 ± 8.51 | 99.53 ± 3.33 |
| Syringic acid | 101.11 ± 7.62 | 71.54 ± 4.81 | 100.34 ± 0.86 |
| P-coumaric acid | 77.88 ± 9.03 | 61.31 ± 5.74 | 99.71 ± 1.48 |

TABLE 6-continued

Detection results of samples prepared in Comparative Examples 1 and 2

| Compound | Comparative Example 1 | Comparative Example 2 | Example 1 |
| --- | --- | --- | --- |
| Sinapic acid | 75.39 ± 7.54 | 83.79 ± 5.58 | 101.90 ± 3.24 |
| Ferulic acid | 66.04 ± 9.65 | 65.29 ± 7.73 | 102.95 ± 1.74 |
| Cinnamic acid | 81.41 ± 5.44 | 67.73 ± 3.57 | 81.31 ± 2.95 |
| Sinapine | 105.80 ± 4.80 | 67.55 ± 8.06 | 97.96 ± 7.90 |

From the results in Table 6, it can be seen that the average recovery rate of polyphenols in the rapeseed oil by the developed method is 81.31% to 102.95%, and the RSDs are 0.86% to 8.03%. Compared with the traditional liquid-liquid extraction and solid-phase extraction, the method developed by the patent has higher accuracy and precision and better extraction effect. Moreover, compared with liquid-liquid extraction and solid-phase extraction, the method not only is simple to operate and low in cost, but also reduces matrix interference by using the $C_{18}$ adsorbent for purification, and the results are more accurate.

Comparative Example 3

Referring to Example 1, the extractant was replaced with pure acetonitrile, and other conditions remained unchanged. The obtained polyphenol extracting solution was detected by liquid chromatography, and the average peak area and RSD were calculated. The results are shown in Table 7.

TABLE 7

Detection results of sample obtained in Comparative Example 3

| Extractant | Caffeic acid/peak area (% RSD) | P-coumaric acid/peak area (% RSD) | Sinapic acid/peak area (% RSD) | Ferulic acid/peak area (% RSD) |
| --- | --- | --- | --- | --- |
| Acetonitrile | 154868(9.34) | 674863(4.80) | 227807(9.01) | 519482(6.05) |
| Acetonitrile and water | 564683(9.93) | 1132224(2.74) | 439369(7.74) | 868811(2.18) |

Comparative Example 4

Referring to Example 1, the adsorbent was replaced with PSA or GCB, respectively, and other conditions remained unchanged. The obtained polyphenol extracting solution was detected by liquid chromatography. The results are shown in Table 8.

TABLE 8

Detection results of sample obtained in Comparative Example 4

| Adsorbent | Caffeic acid/peak area (% RSD) | P-coumaric acid/peak area (% RSD) | Sinapic acid/peak area (% RSD) | Ferulic acid/peak area (% RSD) |
| --- | --- | --- | --- | --- |
| PSA | 138529 (8.78) | 478271 (3.70) | 378770 (4.04) | 606039 (3.64) |
| GCB | 182310 (3.86) | 563629 (4.53) | 412811 (6.74) | 641664 (4.81) |
| $C_{18}$ | 564683 (9.93) | 1132224 (2.74) | 439369 (7.74) | 868811 (2.18) |

Although the disclosure has been disclosed as above in preferred examples, it is not intended to limit the disclosure. Any person skilled in the art can make various changes and modifications without departing from the spirit and scope of the disclosure. The protection scope of the disclosure shall be defined by the claims.

What is claimed is:

1. A method for extracting polyphenols from rapeseed oil, comprising:
   (1) extracting the rapeseed oil by using a mixed solution of acetonitrile and water as an extractant, performing solid-liquid separation, and collecting a supernatant to obtain an extracting solution; and
   (2) adding 20 to 35 mg/mL $C_{18}$ adsorbent to the extracting solution obtained in step (1), performing solid-liquid separation, and collecting a supernatant to obtain a polyphenol solution.

2. The method according to claim 1, wherein a volume ratio of acetonitrile to water in the extractant is (5 to 8):1.

3. The method according to claim 1, wherein a mass-volume ratio of rapeseed oil to extractant in step (1) is 0.15 to 0.35 g/mL.

4. The method according to claim 1, further comprising:
   (1) extracting the rapeseed oil by using the mixed solution of acetonitrile and water as the extractant, and separating extract liquor to obtain the extracting solution, wherein a volume ratio of acetonitrile to water in the extractant is (5 to 8):1, and a mass-volume ratio of rapeseed oil to extractant is 0.15 to 0.35 g/mL; and
   (2) adding 20 to 35 mg/mL $C_{18}$ adsorbent to the extracting solution obtained in step (1), and performing solid-liquid separation to obtain the polyphenol solution.

5. The method according to claim 1, wherein the step (1) further comprises adding anhydrous $MgSO_4$ and NaCl to cooperate with the extractant.

6. The method according to claim 5, wherein a mass ratio of anhydrous $MgSO_4$ to NaCl is 2:1 to 6:1.

7. The method according to claim 1, wherein the step (1) further comprises performing a freezing treatment on separated liquid to obtain the extracting solution.

8. The method according to claim 4, wherein the step (1) further comprises performing a freezing treatment on separated liquid to obtain the extracting solution.

9. The method according to claim 7, wherein the freezing treatment is performed at a temperature of −15° C. to −20° C. for 1.5 to 2.5 h.

10. The method according to claim 8, wherein the freezing treatment is performed at a temperature of −15° C. to −20° C. for 1.5 to 2.5 h.

11. The method according to claim 1, wherein the step (2) further comprises adding anhydrous $MgSO_4$ to be used in combination with the adsorbent, so as to further remove moisture and fatty impurities in the extracting solution to obtain the polyphenol solution.

12. The method according to claim 4, wherein the step (2) further comprises adding anhydrous $MgSO_4$ to be used in combination with the adsorbent, so as to further remove moisture and fatty impurities in the extracting solution to obtain the polyphenol solution.

13. A method for detecting polyphenols in vegetable oil, comprising pre-treating the vegetable oil to obtain a polyphenol solution by using the method according to claim 1, and then performing detection.

14. The method according to claim 13, wherein the detection is liquid chromatography detection.

* * * * *